United States Patent [19]

Guindon et al.

[11] Patent Number: 4,855,481
[45] Date of Patent: Aug. 8, 1989

[54] PROCESS FOR THE PREPARATION OF HMG-COA REDUCTASE INHIBITORS AND INTERMEDIATE COMPOUNDS EMPLOYED THEREIN

[75] Inventors: Yvan Guindon, Closse Ile Bizard; Christiane Yoakim, Montreal; Howard E. Morton, Dollard des Ormeaux, all of Canada

[73] Assignee: Merck & Co., Inc., Rahway, N.J.

[21] Appl. No.: 176,828

[22] Filed: Apr. 4, 1988

Related U.S. Application Data

[62] Division of Ser. No. 875,846, Jun. 18, 1986, abandoned, which is a division of Ser. No. 673,231, Nov. 19, 1984, Pat. No. 4,611,068.

[51] Int. Cl.$^4$ .............................................. C07C 69/76
[52] U.S. Cl. ...................................... 560/55; 560/184; 556/12; 549/292; 549/561
[58] Field of Search .................... 556/437, 12; 560/55, 560/184

Primary Examiner—Glennon H. Hollrah
Assistant Examiner—A. A. Owens
Attorney, Agent, or Firm—Melvin Winokur; Joseph F. DiPrima

[57] ABSTRACT

An intermediate compound of the formula

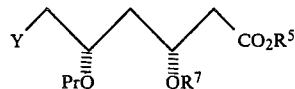

wherein Y is chloro or bromo:
  Pr is a protecting group selected from benzoyl, acetyl, triphenylsilyl or t-butyldiphenylsilyl:
  $R^5$ is $C_{1-5}$ alkyl or benzyl; and
  $R^7$ is $C_{1-5}$ alkyl, benzyl, $C_{2-5}$ *alkoxyalkyl* or $C_{3-5}$ alkoxyalkoxyalkyl,
  useful for the preparation of certain HMG-CoA reductase inhibitors.

2 Claims, No Drawings

PROCESS FOR THE PREPARATION OF HMG-COA REDUCTASE INHIBITORS AND INTERMEDIATE COMPOUNDS EMPLOYED THEREIN

This is a division of application Ser. No. 875,846 filed June 18, 1986 now abandoned which is a division of application Ser. No. 673,231 filed Nov. 19, 1984 now U.S. Pat. No. 4,611,068.

BACKGROUND OF THE INVENTION

Endo et al., *J. Antibiotics, XXIX*, 1346 (1976) described a fermentation product, ML-236B, with potent antihypercholesterolemic activity which acts by inhibiting HMG-CoA reductase. This material, named compactin by Brown et al., *J. Chem. Soc., Perkin I*, 1165 (1976) was shown to have a desmethyl mevalonolactone partial structure and the stereochemistry was studied.

Shortly thereafter a chemically similar, natural product MK-803 (mevinolin), obtained by fermentation, was isolated and characterized, by Monaghan et al., U.S. Pat. No. 4,231,938. It has been shown to have the same desmethyl mevalonolactone partial structure and the absolute stereochemical configuration has been determined and described in EPO publication No. 0,022,478 of Merck & Co., Inc.

Totally synthetic analogs of these natural inhibitors have been prepared and described in Sankyo's U.S. Pat. No. 4,198,425 and Sankyo's U.S. Pat. No. 4,255,444 with no attempt being made to separate the stereo- and optical isomers. Subsequently, as described in Merck's EPO publication No. 0,024,348 and by Meyer, *Ann. Chem.*, (1979), pages 484–491, similar totally synthetic analogs were separated into their stereoisomers and optical enantiomers. Furthermore, it was shown in EPO publication No. 0,024,348 that essentially all of the HMG-CoA reductase activity resides in the 4(R)-trans species as is the case with the naturally occurring compounds compactin and mevinolin.

In most of the prior art process for preparing the totally synthetic compounds, the lactone moiety of each compound had to be elaborated by a lengthy series of synthetic operations followed by very tedious and expensive chromatographic separation of the cis, trans racemates, or enantiomers, following which, the inactive cis-isomer would be discarded.

A process for the preparation of the lactone ring system in the correct optically active form was recently reported by Majewski et al., *Tetrahedron Lett.*, 1984, 2101–2104 utilizing a (3S,5S) iodoketal of the following formula:

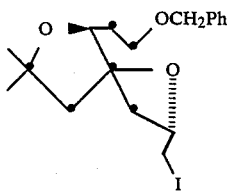

DETAILED DESCRIPTION OF THE INVENTION

This invention relates to a novel process for the preparation of antihypercholesterolemic agents of the following general structural formula (I):

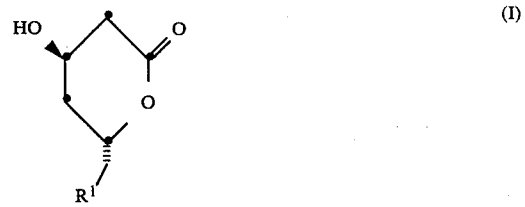

wherein $R^1$ is selected from the group consisting of:

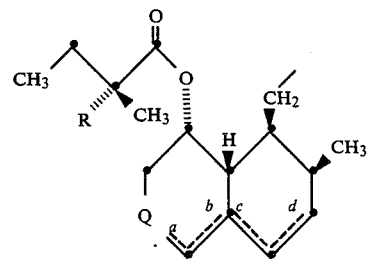

wherein Q is

or

$R^6$ is H or OH;

R is hydrogen or methyl, and a, b, c, and d represent optional double bonds, especially wherein b and d represent double bonds or a, b, c, and d are all single bonds; or

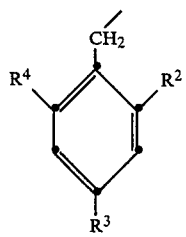

wherein $R^2$ and $R^3$ are independently $C_{1-3}$ alkyl or halo (F, Cl or Br) and $R^4$ is hydrogen, phenyl, benzyloxy, substituted phenyl or substituted benzyloxy in which the phenyl group in each case is substituted with one or more substituents selected from $C_{1-3}$ alkyl and halo, which comprises:

(A) reacting a compound of the formula (II):

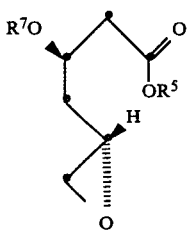

wherein $R^5$ is $C_{1-5}$ alkyl or benzyl and $R^7$ is $C_{1-5}$ alkyl, benzyl, $C_{2-5}$ alkoxyalkyl, such as $CH_3OCH_2$, or $C_{3-6}$ alkoxyalkoxyalkyl, such as $CH_3OCH_2CH_2OCH_2$, with a compound of the formula (III):

$$R^1X \qquad (III)$$

wherein $R^1$ is defined above, X is a metal atom or metal complex selected from Li, MgCl, MgBr, $(CuMgCl)_{1/2}$ or $(CuMgBr)_{1/2}$ or an alkali metal (Li, Na, or K) plus an aryl sulfonyl group selected from

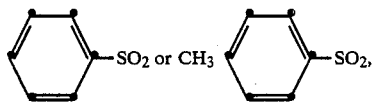

followed by the removal of the aryl sulfonyl group [Trost et al. *Tetrahedron Lett.*, 1976, 3477] to afford a compound of the formula (IV):

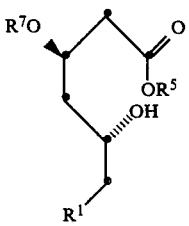

(B) lactonizing the compound of the formula (IV) under standard acidic conditions to afford the compound of formula (V):

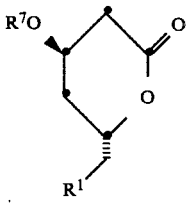

and (C) removing the $R^7$ group by suitable methods known in the art [T. Greene, *Protective Groups In Organic Synthesis*, John Wiley & Sons, 1981, pp 10-86] or with an organoboron halide to afford the compound of formula (I).

In a preferred embodiment, the compounds prepared by the process of this invention are those compounds of the formula (I) wherein $R^1$ is (a) and $R^6$ is hydrogen and R is hydrogen or methyl and b and d represent double bonds or a, b, c and d are single bonds.

In a second preferred embodiment, the compounds prepared by the process of this invention are those compounds of the formula (I) wherein $R^1$ is (b), $R^2$ and $R^3$ independently are chloro, fluoro or methyl and $R^4$ is hydrogen, 4-fluoro-3-methylphenyl or 4-fluorobenzyloxy. The most preferred compounds are those wherein (1) $R^2$ and $R^3$ are methyl and $R^4$ is 4-fluoro-3-methylphenyl; (2) $R^2$ and $R^3$ are methyl and $R^4$ is 4-fluorobenzyloxy; and (3) $R^2$ and $R^3$ are chloro and $R^4$ is hydrogen.

The reaction of the compound of the formula (II) with the compound of the formula (III) is conducted at a temperature between −78° and 0° C., preferably at −78° C. with warming to −20° C. for a period of from 1 to 12 hours, most preferably 1 hour at −78° C. and 1 hour at −23° C., in a inert solvent. Illustrative of such inert solvents are: ethers or thioethers or mixtures thereof, such as diethyl ether, tetrahydrofuran, dimethoxyethane, dimethylsulfide and the like.

The amounts of reactants that are employed in this reaction may vary between 0.1 and 1.0 equivalents of the compound of the formula (II) to each equivalent of the compound of the formula (III). However, 0.4 equivalents of the compound of the formula (II) is preferred. The compound of the formula (III) wherein X is $(CuMgBr)_{1/2}$ is a preferred reactant.

The lactonization of the compound of the formula (IV) is conducted at a temperature between 0° and 25° C., preferably at ambient temperature, for a period of from 1 to 12 hours, preferably 3 hours in an inert solvent with a catalytic amount of an acid. Illustrative of such inert solvents are: hydrocarbons, such as hexane, toluene, benzene, cyclohexane and the like; and ethers, such as, diethylether, tetrahydrofuran, dimethoxyethane and the like. Illustrative of such acids are organic acids, such as, p-toluenesulfonic, benzenesulfonic and the like and inorganic acids, such as, hydrochloric. The preferred acid utilized in the lactonization is p-toluenesulfonic acid.

The removal of the $R^7$ protecting group is conducted at a temperature between −78° and 0° C., preferably at −78° for a period from 1 to 12 hours, preferably 1 hour in an inert solvent in the presence of an organoboron halide. Illustrative of such inert solvents are: chlorinated hydrocarbons, such as, methylene chloride, chloroform, dichloroethane or low melting mixtures thereof and the like.

The organoboron halide reactant is represented by the following formula:

$$R^8R^9BY$$

wherein $R^8$ and $R^9$ independently are $C_{1-4}$ alkyl, phenyl or when taken together with the boron atom to which they are attached form a 5, 6 or 7 membered ring or a bicyclic ring and Y is chloro or bromo. The preferred organoboron halide is dimethylboron bromide. The amount of the organoboron halide utilized may vary between 1 and 10 equivalents for each equivalent of the compound of the formula (V), with 4 equivalents being preferred.

The starting materials are either known or readily prepared according to the synthetic pathways described below.

For compounds of the formula (III) wherein $R^1$ is (a) and X is a metal atom or metal complex, *Tetrahedron Lett.*, pp. 1373-6 (1983) describes a procedure for preparing compounds which can be readily converted into the desired compounds of the formula (III) using standard reaction conditions. For compounds of the formula (III) wherein X is

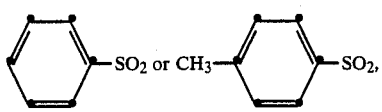

*Tetrahedron Lett.*, pp. 1655–8 (1984) describes a procedure for preparing compounds which can be readily converted into the desired compounds of the formula (III) using standard conditions. The compounds of the formula (III) wherein $R^1$ is (b) are known in the art.

The compound of the formula (II) wherein $R^5$ and $R^7$ are described above are readily prepared according to the following synthetic pathway from (S)-malic acid:

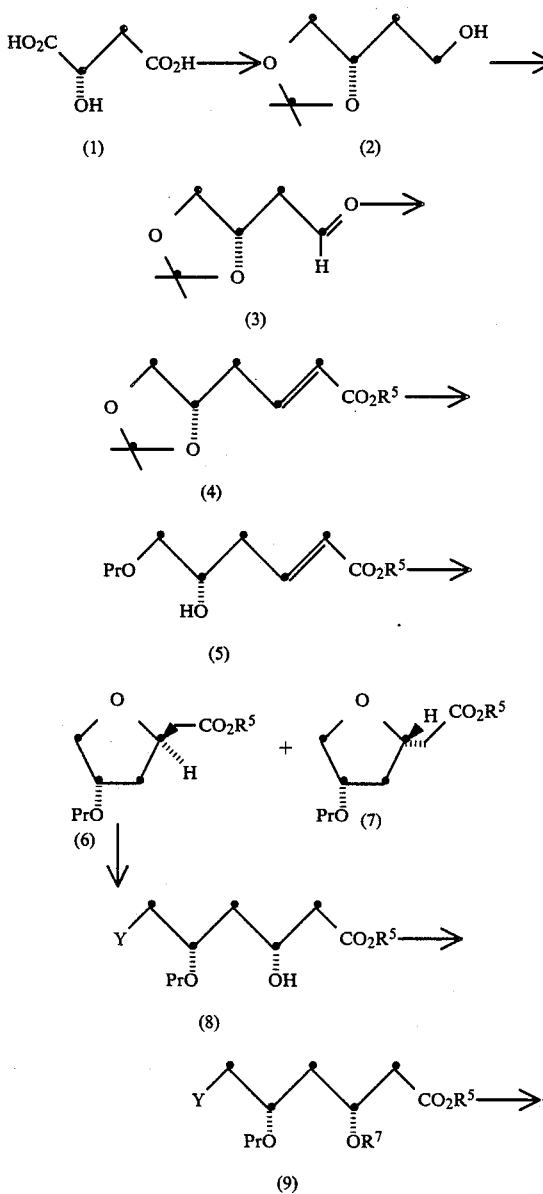

(S)-Malic acid (1) is reduced under standard reduction conditions using $BH_3.THF$ and then ketalized with acetone to give compound (2). Compound (2) is subjected to Swern oxidation to yield compound (3), which, without isolation, is treated under Wittig conditions with $Ph_3PCHCO_2R^5$ to give Compound (4). Compound (4) is hydrolyzed under acid conditions and selectively protected to give Compound (5) wherein Pr is a protecting group selected from benzoyl, acetyl, triphenylsilyl or tert-butyldiphenylsilyl, preferably t-butyldiphenylsilyl. Compound (5) is [1]cyclized to Compounds (6) and (7) under basic conditions with concomitant migration of the Pr group. Compound (7) may be isomerized to the desired Compound (6) under basic conditions. Compound (6) is converted to Compound (8) using an organoboranhalide $R^8R^9BY$, preferably dimethylboron bromide. Compound (8) is treated with $R^7$-halide to get Compound (9) which is treated with tetraalkylammonium fluoride oranalkalimetal alkoxide to afford the compound of formula (II).

The following Examples illustrate the present invention and as such are not to be considered as limiting the invention set forth in the claims appended hereto.

EXAMPLE 1

Step (a)

Preparation of (S)-1,2-O-Isopropylidenebutane-1,2,4-triol

To a cold (0° C.), well-stirred solution of (S)-malic acid (13.4 g, 100 mmol) in 300 ml dry tetrahydrofuran, under argon, was added dropwise (via capillary) a tetrahydrofuran solution of borane-THF complex (300 ml, 300 mmol) over a period of 3 hours. The cooling bath was removed and the resultant slurry was stirred at room temperature for 15 hours. The reaction mixture was then cooled to 0° C. and carefully treated with dry methanol (100 ml). After warming to room temperature, the solvent was evaporated. The residue was evaporated three times with dry methanol (100 ml each) to ensure complete methanolysis of the reduction intermediate. Brief drying (0.1 mm) gave 10.3 g of the crude triol.

This material was dissolved in acetone (300 ml) and a catalytic amount of p-TsOH.H$_2$O (0.95 g, 5 mmol) added. After 12 hours at room temperature the reaction mixture was quenched with triethylamine (0.70 ml, 5 mmol) and concentrated. The resultant oil was dissolved in ether (400 ml) and washed with water (3×50 ml) and brine (50 ml) and dried over MgSO$_4$. Concentration and bulb-to-bulb distillation of the residue (air-bath temperature 85°–95° C., 0.15 mm; lit.[1] 55°–61° C., 0.05 mm) gave 11.7 g (80%) of the desired product. $^1$H NMR (CDCl$_3$) analysis showed that this material contained <10% of the isomeric acetonide (S)-2,4-O-isopropylidene butane-1,2,4-triol[1,2] and was used without further purification. This material exhibited IR (film) 3450, 2950, 1380 and 1050 cm$^{-1}$; $^1$H NMR (250 MHz, CDCl$_3$) δ1.38 (s, 3H), 1.43 (s, 3H), 1.79−1.88 (m, 2H), 2.55 (broad s, 1H), 3.61 (d,d, J=7.7 Hz, 1H), 3.80 (t, J-5.9 Hz, 2H), 4.10 (d,d J=7.0, 7.7 Hz, 1H), 4.28 (m, 1H).

[1] A. I. Meyers and J. P. Lawson, *Tetrahedron Lett.*, 23, 4883 (1982).
[2] S. Hanessian, A. Ugolini and M. Therien, *J. Org. Chem.*, 48, 4427 (1983).

Step (b)

Preparation of Ethyl (E)-(S)-O-Isopropylidene-5,6-dihydroxy-2-hexenoate

A cold (−78° C.) stirred solution of oxalyl chloride (1.92 ml, 22 mmol) in 50 ml of dry methylene chloride, under argon, was treated with a solution of DMSO (3.55 ml, 25 mmol) in the same solvent (10 ml). After stirring at −78° C. for 10 minutes a solution of (S)-1,2-O-isopropylidene butane-1,2,4-triol (2.92 g, 20 mmol) in 15 ml of methylene chloride was added. The resultant slurry was stirred at −78° C. for 40 minutes, then treated with diisopropylethylamine (17.5 ml, 100 mmol). The cooling bath was removed and the reaction mixture was stirred at room temperature for 1 hour to afford a yellow solution of (S)-O-isopropylidene 4-oxybutane-1,2-diol.

This solution was cooled to 0° C. and treated with carbethoxymethylenetriphenylphosphorane (17.4 g, 50 mmol) at 0° C. for 1 hour and at room temperature for 4 hours. The resultant solution was diluted with ether (300 ml), washed with water (3×50 ml), 10% aqueous NaHSO$_4$ (50 ml) and brine (2×50 ml) and dried over MgSO$_4$. Removal of solvent gave a viscous oil. Ether (150 ml) and hexane (150 ml) were added and the mixture kept at −10° C. for 15 hours. Filtration of the white precipitate (Ph$_3$P=O) and removal of solvent gave the crude product. Flash chromatography (hexane-ethyl acetate 85:15) gave 3.60 g (84%) of ethyl (E)-(S)-O-isopropylidene-5,6-dihydroxy-2-hexenoate: $[\alpha]_D$ −18.0 (c 2.43, MeOH); IR (film) 2994, 1727, 1661, 1372, 1269, 1172 and 1064 cm$^{-1}$; $^1$H NMR (CDCl$_3$) δ1.30 (t, J=7.0 Hz, 3H), 1.36 (s, 3H), 1.43 (s, 3H), 2.39–2.60 (m, 2H), 3.59 (m, 1H), 4.07 (m, 1H), 4.16–4.30 (buried m, 1H), 4.20 (q, J=7.0 Hz, 2H), 5.92 (d,t, J=15.5, 1.5 Hz, 1H), 6.92 (d,t, J=15.5, 7.2 Hz); MS m/e (relative intensity) 199 (43), 101 (100).

Anal. calcd. for C$_{11}$H$_{18}$O$_4$: C, 61.66; H, 8.47. Found: C, 61.42; H, 8.44.

Step (c)

Preparation of Ethyl (E)-(S)-5,6-dihydroxy-2-hexenoate

To a solution of ethyl-(E)-(S)-O-isopropylidene-5,6-dihydroxy-2-hexenoate (5.35 g, 25 mmol) in 100 ml tetrahydrofuran was added 1N HCl (66 ml). The reaction mixture was stirred at room temperature for 18 hours. NaCl (10 g) and ethyl acetate (400 ml) were added. The organic layer was separated and washed with brine (2×50 ml). The aqueous washings were extracted with ethyl acetate (2×100 ml), the extracts washed with brine (25 ml) and the organic layers combined. Drying (MgSO$_4$) and removal of solvent gave 4.04 g (93%) of a viscous oil. This material exhibited: IR (film) 3400, 1720, 1657 and 1040 cm$^{-1}$; $^1$H NMR (CDCl$_3$) δ1.28 (t, J=7.0 Hz, 3H), 2.25 (broad s, 1H), 2.39 (m, 2H), 2.58 (broad s, 1H), 3.43–3.55 (m, 1H), 3.63–3.73 (m, 1H), 3.81–3.92 (m, 1H), 4.18 (q, J=7.0 Hz, 2H), 5.91 (d, J=16 Hz, 1H), 6.96 (dt, J=16, 6.6 Hz, 1H).

Anal. calcd. for C$_8$H$_{14}$O$_4$: C, 55.16; H, 8.10. Found: C, 55.52; H, 8.08.

Step (d)

Preparation of Ethyl (E)-(S)-6-t-butyldiphenylsiloxy-5-hydroxy-2-hexenoate

To a cold (0° C.), stirred solution of the diol from Step (c) (4.04 g, 23.2 mmol) in 116 ml dry methylene chloride, under argon, was sequentially added diisopropylethylamine (6.08 ml, 34.8 mmol) 4-dimethylamino pyridine (280 mg, 2.3 mmol) and t-butyldiphenylsilyl chloride (7.54 ml, 29 mmol). The reaction mixture was stirred at 0° C. for 1 hour and then at room temperature for 18 hours. Water (100 ml) and ether (400 ml) were added. The organic layer was separated, washed with water (100 ml), saturated aqueous NaHCO$_3$ (50 ml), 10% aqueous NaHSO$_4$ (50 ml), and brine (50 ml). Drying (MgSO$_4$) and removal of solvent gave the crude product. Purification by flash chromatography (300 g, SiO$_2$, hexane-ethyl acetate 85:15) gave 9.41 g (98%) of essentially pure mono-siloxy alcohol. This material exhibited: $[\alpha]_D$ −10.0 (c 1.23, MeOH); IR (film) 3480, 2940, 1723, 1658, 1594, 1431, 1114 and 704 cm$^{-1}$; $^1$H NMR (CDCl$_3$) δ1.07 (s, 9H), 1.28 (t, J=7.2 Hz, 3H), 2.36 (broad t, J=6.5 Hz, 2H), 2.53 (d, J=4.4 Hz, 1H), 3.53 (d,d, J=10.2, 6.7 Hz, 1H), 3.67 (d,d, J=10.2, 3.7 Hz, 1H), 3.85 (m, 1H), 4.18 (q, J=7.2 Hz, 2H), 5.87 (d, J=15.5 Hz, 1H), 6.94 (d,d, J=15.5, 7.3 Hz, 1H), 7.34–7.49 (m, 6H), 7.60–7.68 (m, 4H); MS m/e (relative intensity) 355 (5), 199 (100).

Anal. calcd. for C$_{24}$H$_{34}$O$_4$Si: C, 69.87; H, 7.82. Found: C, 70.22; H, 7.60.

Step (e)

Preparation of Ethyl 2(R)-(4(S)-tert-butyldiphenylsiloxytetrahydrofuran)acetate and its 2(S),4(S)-isomer To a cold (0° C.), stirred solution of ethyl (E)-(S)-6-tert-butyldiphenylsiloxy-(5)-hydroxy-2-hexenoate (9.41 g, 23.0 mmol) in 200 ml dry ethanol, under argon, was added a solution of sodium ethoxide (2.3 mmol) in ethanol (30 ml). Stirring was continued at room temperature for 2 hours and at 65° C. for 4 hours. The reaction mixture was then cooled to room temperature and quenched with acetic acid (2.3 mmol). Concentration provided the crude product as a yellow oil (9.5 g). TLC (hexane-ethyl acetate, 4:1) and $^1$H NMR (250 MHz, CDCl$_3$) analyses of the crude product indicated the pressure of the desired β (R$_f$0.55) and α (R$_f$0.53) product isomers in a ratio of 2:1 along with a small amount of starting material. This material was purified in two batches by careful flash chromatography (300 g SiO$_2$, eluant:hexane-ethyl acetate, 95:5) to afford after concentration of the appropriate fractions 4.51 g of pure 2(R),4(S)-β-isomer.

Further elution of the column (hexane-ethyl acetate, 4:1) and combination of the appropriate fractions gave 4.80 g of a mixture of the 2(R),4(S)- and 2(S),4(S)-isomers along with a small amount of starting material. This material was dissolved in ethanol (160 ml) and resubjected to the equilibration conditions (1.16 mmol NaOEt) at 65° C. for 5 hours. Work-up and purification as outlined above (300 g SiO$_2$, eluant:hexane-ethyl acetate, 95:5 then 4:1) gave 2.27 g of pure 2(R),4(S)-β-isomer (total yield 6.77 g, 72%). $[\alpha]_D$ 7.81 (c 2.08, MeOH), IR (film) 3080, 2940, 1738, 1593, 1115 and 703 cm$^{-1}$; $^1$H NMR (250 MHz, CDCl$_3$) δ1.06 (s, 9H), 1.26 (t, J=7.2 Hz, 1H), 1.55 (d,d,d, J=15.4, 9.6, 5.6 Hz, 1H), 2.07 (d,d,d, J=15.4, 5.6, 1.8 Hz, 1H), 2.44 (d,d, J=15.4, 5.9 Hz, 1H), 2.57 (d,d, J=15.2, 7.2 Hz, 1H), 3.72 (d,d,d, J=9.4, 2.6, 0.8 Hz, 1H), 3.84 (d,d, J=9.4, 4.6 Hz, 1H), 4.15 (q, J=7.2 Hz, 2H), 4.45 (m, 1H), 4.57 (m, 1H), 7.33–7.50 (m, 6H), 7.60–7.76 (m, 4H); MS m/e (relative intensity) 355 (11), 199 (100).

Anal. calcd. for C$_{24}$H$_{32}$O$_4$Si: C, 69.87; H, 7.82. Found: C, 70.15; H, 7.73.

Further elution of the column (hexane-ethyl acetate, 4:1) collection of the appropriate fractions gave 0.98 g (10%) of the 2(S),4(S)-α-isomer. IR (film) 3081, 2942, 1738, 1593, 1113 and 705 cm$^{-1}$; $^1$H NMR (250 MHz, CDCl$_3$) δ1.07 (s, 9H), 1.27 (t, J=7.2 Hz, 3H), 1.75

(d,d,d,d, J=13.1, 5.7, 3.4, 0.9 Hz, 1H), 2.16 (d,d,d, J=13.1, 7.5, 6.3 Hz, 1H), 2.66 (d,d, J=15.4, 6.4 Hz, 1H), 2.84 (d,d, J=15.4, 7.3 Hz, 1H), 3.62 (d,d, J=9.4, 4.9 Hz, 1H), 3.81 (d,d,d, J=9.4, 2.8, 0.9 Hz, 1H), 4.16 (q, J=7.2 Hz, 2H), 4.31 (m, 1H), 4.43 (m, 1H), 7.33–7.50 (m, 6H), 7.62–7.77 (m, 4H); MS m/e (relative intensity) 367 (14), 355 (100), 199 (61).

*1.01 g (11%) of a mixture of the β- and α-isomers was also recovered.

Step (f)

Preparation of Ethyl 6-bromo-5(S)-tertbutyldiphenylsiloxy-3(R)-hydroxyhexanoate To a cold (0° C.), stirred mixture of ethyl 2(R)-(4(S)-tert-butyldiphenylsiloxytetrahydrofuran)acetate (1.21 g, 2.93 mmol) and diisopropylethylamine (51 μl, 0.29 mmol) in 16.5 1 ml dry methylene chloride, under argon, was added a solution of dimethylboron bromide (3.46 ml, 5.98 mmol) in methylene chloride. The reaction mixture was then stirred at room temperature for 2 hours, diluted with ether (100 ml) and quenched with saturated aqueous NaHCO$_3$ (10 ml). The organic layer was separated, washed with 10 ml portions of saturated aqueous NaHCO$_3$, water and brine and dried over MgSO$_4$. Removal of solvent gave a yellow oil which was subjected to flash chromatography on silica gel (eluant:hexane-ethyl acetate, 4:1) to afford 1.19 g (82%) of the purified product as a colorless oil. This material exhibited [α]$_D$ +2.81 (c 1.67, MeOH); IR (film) 3430, 2938, 1725, 1590, 1430, 1112 and 700 cm$^{-1}$; $^1$H NMR (250 MHz, CDCl$_3$) δ1.08 (s, 9H), 1.26 (t, J=7.2 Hz, 3H), 1.82 (m, 2H), 2.30 (m, 2H), 3.05 (broad s, 1H), 3.39 (d, J=3.7 Hz, 2H), 4.10 (m, 1H), 4.15 (q, J=7.2 Hz, 2H), 7.34–7.48 (m, 6H), 7.64–7.70 (m, 4H); MS m/e (relative intensity) 447 (4), 435 (2), 199 (100).

Anal. calcd. for C$_{24}$H$_{33}$O$_4$SiBr: C, 58.41; H, 6.74. Found: C, 58.19; H, 6.73.

Step (g)

Preparation of Ethyl 6-bromo-5(S)-tert-butyldiphenylsiloxy-(3)-(R)-(methoxymethoxy)hexanoate To a cold (−10° C.), stirred solution of ethyl 6-bromo-5(S)-tert-butyldiphenylsiloxy-(3)-(R)-hydroxyhexanoate (0.84 g, 1.70 mmol) in 5.15 ml of dry acetonitrile, under argon, were sequentially added diisopropylethylamine (0.89 ml, 5.10 mmol), 4-N,N-dimethylaminopyridine (21 mg, 0.17 mmol) and chloromethyl methyl ether (1.03 ml, 13.6 mmol). The argon inlet was removed and the reaction mixture was stored at −3° C. for 24 hours. The reaction mixture was then quenched with saturated (aqueous) NaHCO$_3$ (3 ml) and diluted with ether (60 ml). The organic layer was separated, washed with saturated aqueous NaHCO$_3$ (2×10 ml), water (10 ml), 10% aqueous NaHSO$_4$ (10 ml) water (10 ml) and brine (10 ml). Drying (MgSO$_4$) and concentration gave a pale yellow oil. Purification by flash chromatography on silica gel (60 g, eluant:hexane-ethyl acetate, 4:1) provided 0.85 g (94%) of pure product. This material exhibited: [α]$_D$=0.77 (c 1.68, CHCl$_3$): IR (film) 3075, 2935, 1738, 1589, 1428, 1031 and 701 cm$^{-1}$; $^1$H NMR (250 MHz, CDCl$_3$) δ1.08 (s, 9H), 1.24 (t, J=7.1 Hz, 3H), 1.94 (broad t, J=6.0 Hz, 2H), 2.26 (d,d, J=15.3, 5.2 Hz, 1H), 2.39 (d,d, J=15.3, 7.3 Hz, 1H), 3.18 (s, 3H), 3.37 (d, J=4.3 Hz, 2H), 3.92 (m, 1H), 4.04 (m, 1H), 4.12 (q, J=7.1 Hz, 2H), 4.50 (d, J=7.1 Hz, A part of AB, 1H), 4.58 (d, J=7.1 Hz, B part of AB, 1H), 7.33–7.46 (m, 6H), 7.65–7.74 (m, 4H); MS m/e (relative intensity) 479 (28), 213 (100).

Anal. calcd. for C$_{26}$H$_{37}$O$_5$SiBr: C, 58.09; H, 6.97; Br, 14.86. Found: C, 58.33; H, 7.02; Br, 14.79.

Step (h)

Preparation of Ethyl 5(S),6-epoxy-3(R)-(methoxymethoxy)hexanoate

A cold (0° C.), stirred solution of ethyl 6-bromo-5(S)-tert-butyldiphenylsiloxy-3(R)-(methoxymethoxy)hexanoate (0.80 g, 1.49 mmol) in 3.8 ml dry tetrahydrofuran (THF), under argon, was treated with a solution of tetra-n-butylammonium fluoride (4.47 ml, 4.47 1 mmol; 1.0M solution in THF). The cooling bath was removed and the reaction mixture was stirred at room temperature for 3 hours. Ether (50 ml) was then added and the mixture washed with water (5 ml), 10% aqueous NaHSO$_4$ (5 ml), water (5 ml) and brine (5 ml). Drying (MgSO$_4$) and removal of solvent gave a pale yellow oil which was subjected to flash chromatography on silica gel (20 g, hexane-ethyl acetate, 4:1) to provide 0.241 g (74%) of the desired epoxide, [α]$_D$ 31.5 (c 0.98, MeOH). IR (film) 2938, 1736 and 1035 cm$^{-1}$; $^1$H NMR (250 MHz, CDCl$_3$) α1.23 (t, J=7.2 Hz, 3H), 1.70–1.82 (m, 1H), 1.86–1.99 (m, 1H), 2.49 (m, 1H), 2.56 (d,d, J=15.6, 5.0 Hz, 1H), 2.71 (d,d, J=15.6, 6.0 Hz, 1H), 2.77 (m, 1H), 3.08 (m, 1H), 3.38 (s, 3H), 4.16 (q, J=7.2 Hz, 2H), 4.29 (m, 1H), 4.67 (d, A part of AB, J=7.8 Hz, 1H), 4.72 (d, B part of AB, J=7.8 Hz, 1H).

Anal. calcd. for C$_{10}$H$_{18}$O$_5$: C, 55.03; H, 8.31. Found: C, 54.82; H, 8.39.

EXAMPLE 2

Step (a)

Preparation of 2,4-Dichlorobenzylmagesium bromide

To stirred magnesium metal (0.121 g, 5 mmol) in 1.0 ml of dry ether, under argon, was added 0.5 ml of an ether solution of 2,4-dichlorobenzyl bromide (1.20 g, 5 mmol in 4.0 ml dry ether). A small crystal of iodine was added and initiation of the reaction took place (exothermic) within 5 minutes. The remaining solution of 2,4-dichlorobenzyl bromide was then added dropwise at such a rate as to maintain a mild reflux. After the addition was complete the reaction mixture was refluxed for 1 hour to afford a colorless solution of 2,4-dichlorobenzylmagnesium bromide in ether (about 1.0M).

Step (b)

Preparation of Ethyl 7-(2,4-dichlorophenyl-5(R)-hydroxy-3(R)-(methoxymethoxy)heptanoate To a cold (−78° C.), stirred suspension of cuprous bromide-dimethyl sulfide complex (88 mg. 0.43 mmol) in a mixture of dimethyl sulfide (1.3 ml) and ether (0.4 ml), under argon, was added dropwise a solution of 2,4-dichlorobenzylmagnesium bromide (0.88 ml, 0.88 mmol; 1.0M in ether). The resultant orange solution was stirred at −78° C. for 15 minutes. A solution of ethyl 5(S),6-epoxy-3(R)-(methoxymethoxy)hexanoate (72 mg, 0.33 mmol) in 0.5 ml dry ether was then added dropwise over a period of 3 minutes. The reaction mixture was stirred at −78° C. for 1 hour and at −23° C. for 1 hour. Saturated aqueous NH$_4$Cl (0.5 ml) adjusted to pH 8 with concentrated NH$_4$OH, and ether (20 ml) were added. After warming to room temperature the organic layer was separated, washed with 5 ml portions of saturated aqueous NH4Cl (pH 8), water and brine and dried over MgSO4. Concentration and purification by flash chromatography on silica gel (eluant:hexane-ethyl acetate, 7:3) gave pure product, 124 mg (100%). This material exhibited: $[\alpha]_D + 5.37$ (c 0.85, MeOH); IR (film) 3480, 2943, 1738, 1591, 1477 and 1136 cm$^{-1}$; $^1$H NMR (250 MHz, CDCl3) δ1.26 (t, J=7.2 Hz, 3H), 1.66–1.87 (m, 4H), 2.50 (d,d, J=15.0, 6.4 Hz, 1H), 2.71 (d,d, J=15.0, 6.3 Hz, 1H), 2.74–2.96 (m, 2H), 3.11 (broad s, 1H), 3.39 (s, 3H), 3.80 (m, 1H), 4.14 (q, J=7.2 Hz, 2H), 4.22 (m, 1H), 4.69 (d, A part of AB, J=6.7 Hz, 1H), 4.75 (d, B part of AB, J=6.7 Hz), 7.18 (m, 2H), 7.34 (m, 1H); MS m/e (relative intensity) 159 (100).

Anal. calcd. for $C_{17}H_{24}O_5Cl_2$: C, 53.84; H, 6.38. Found: C, 53.91; H, 6.50.

Step (c)

Preparation of 6(R)-[2-(2,4-dichlorophenyl)ethyl]-4(R)-(methoxymethoxy)tetrahydro-2H-pyran-2-one A mixture of 7-(2,4-dichlorophenyl)-5(R)-hydroxy-3(R)-(methoxymethoxy)heptanoate (100 mg, 0.26 mmol) and p-TsOH.H2O (5 mg, 0.026 mmol) in 1.30 ml benzene, under argon, was stirred at room temperature for 3 hours. The reaction mixture was then diluted with either (20 ml), washed with 2 ml portions of saturated aqueous NaHCO3, water and brine and dried over MgSO4. Concentration and purification of the residue by flash chromatography (eluant:hexane-ethyl acetate, 4:1) afforded 78 mg (90%) of the desired lactone, $[\alpha]_D + 32.4$ (c 0.71, MeOH). IR (film) 2940, 1740, 1590, 1475 and 1040 cm$^{-1}$; $^1$H NMR (250 MHz, CDCl3) δ1.75 (m, 1H), 1.94 (m, 2H), 2.07 (m, 1H), 2.65–3.05 (m, 4H), 3.35 (s, 3H), 4.20 (m, 1H), 4.63 (m, 1H), 4.67 (s, 2H), 7.19 (s, 2H), 7.37 (s, 1H); MS m/e (relative intensity) 332 (13), 159 (100).

Step (d)

Preparation of 6(R)-[2-(2,4-dichlorophenyl)ethyl]-4(R)-hydroxy-tetrahydro-2H-pyran-2-one To a cold (−78° C.), stirred solution of the corresponding methoxymethyl ether derivative from Step (c) (65 mg, 0.20 mmol) in 1.50 ml dry methylene chloride, under argon, was added a solution of dimethylboron bromide (1.56M) (0.51 ml, 0.80 mmol) in methylene chloride. Stirring was continued at −78° C. for 1 hour. The reaction mixture was then added to a room temperature stirred mixture of tetrahydrofuran (2.0 ml) and saturated aqueous NaHCO3 (2 ml). After 3 minutes ether (20 ml) was added and the organic layer washed with 2 ml portions of saturated aqueous NaHCO3, water and brine. Drying (MgSO4) and concentration gave the crude product. Purification by flash chromatography (6 g, SiO2, eluant:hexane-ethyl acetate, 4:1) gave 46 mg (79%) of the desired product, $[\alpha]_D + 59.7$ (c 1.10, CHCl3). IR (film) 3440, 1728, 1476, 1260 and 1050 cm$^{-1}$; $^1$H NMR (250 MHz, CDCl3) δ1.78 (m, 1H), 1.88–2.10 (m, 3H), 2.20 (d, J=3.6 Hz, 1H), 2.64 (d,d,d, J=16, 3.4, 0.9 Hz, 1H), 2.76 (d,d, J=16, 4 Hz, 1H), 2.77–3.05 (m, 2H), 4.41 (broad m, 1H), 4.71 (broad m, 1H), 7.18 (s, 2H), 7.36 (s, 1H); MS m/e (relative intensity) 288 (15), 159 (100).

Anal. calcd. for $C_{13}H_{14}O_3Cl_2$: C, 54.00; H, 4.88. Found: C, 54.02; H, 4.89.

EXAMPLES 3–12

Utilizing the general procedures of Example 2 and starting from the appropriately substituted compounds of the formula (III) and ethyl 5(S),6-epoxy-3(R)-(methoxymethoxy)hexanoate the following compounds of the formula (I) are prepared:

| Compound Number | R$^1$ |
| --- | --- |
| 3 | (structure) |
| 4 | (structure) |
| 5 | (structure) |
| 6 | (structure) |
| 7 | (structure) |

What is claimed is:

1. A compound of the formula

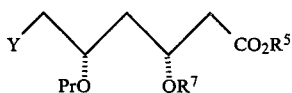

wherein Y is chloro or bromo;
Pr is a protecting group selected from benzoyl, acetyl, triphenylsilyl or t-butyldiphenylsilyl;
$R^5$ is $C_{1-5}$ alkyl or benzyl; and
$R^7$ is $C_{1-5}$ alkyl, benzyl, $C_{2-5}$ alkoxyalkyl or $C_{3-5}$ alkoxyalkoxyalkyl.

2. A compound of claim 1 which is ethyl 6-bromo-5(S)-tert-butyldiphenylsilyloxy-3(R)-(methoxymethoxy)hexanoate.

* * * * *

UNITED STATES PATENT AND TRADEMARK OFFICE
CERTIFICATE OF CORRECTION

PATENT NO. : 4,855,481

DATED : August 8, 1989

INVENTOR(S) : Y. Guindon et al

It is certified that error appears in the above-identified patent and that said Letters Patent is hereby corrected as shown below:

Title page, Item [73], the Assignee should be -- Merck Frosst Canada, Inc., Kirkland, Canada --.

Signed and Sealed this

Twenty-first Day of August, 1990

Attest:

HARRY F. MANBECK, JR.

*Attesting Officer*     *Commissioner of Patents and Trademarks*